United States Patent
Teirstein

(12)
(10) Patent No.: US 6,585,715 B1
(45) Date of Patent: Jul. 1, 2003

(54) IRRADIATION CATHETER AND METHOD OF USE

(76) Inventor: Paul S. Teirstein, 1515 Coast Walk, La Jolla, CA (US) 92037

( * ) Notice: Subject to any disclaimer, the term of this patent is extended or adjusted under 35 U.S.C. 154(b) by 227 days.

(21) Appl. No.: 09/627,920

(22) Filed: Jul. 28, 2000

Related U.S. Application Data

(62) Division of application No. 09/034,138, filed on Feb. 20, 1998, now Pat. No. 6,196,996, which is a continuation-in-part of application No. 08/643,788, filed on May 6, 1996, now Pat. No. 5,891,091, which is a continuation of application No. 08/298,053, filed on Aug. 30, 1994, now Pat. No. 5,540,659, which is a continuation-in-part of application No. 08/231,423, filed on Apr. 22, 1994, now Pat. No. 5,472,425, which is a continuation-in-part of application No. 08/197,970, filed on Feb. 17, 1994, now Pat. No. 5,468,225, which is a continuation of application No. 08/092,332, filed on Jul. 15, 1993, now Pat. No. 5,336,184.

(51) Int. Cl.[7] ...................... A61M 31/00; A61M 29/00; A61B 18/18; A61N 5/00
(52) U.S. Cl. .................. 604/508; 604/103.01; 604/104; 606/7; 600/3
(58) Field of Search .......................... 604/52–53, 96.01, 604/101–105, 171, 500, 507–509; 606/192, 194, 2, 7, 13–14, 32–34; 600/3, 7, 8

(56) References Cited

U.S. PATENT DOCUMENTS

| | | |
|---|---|---|
| 4,183,102 A | 1/1980 | Guiset |
| 4,762,129 A | 8/1988 | Bonzel |
| 4,771,777 A | 9/1988 | Horzewski et al. |
| 4,819,751 A | 4/1989 | Shimada et al. |
| 4,909,781 A | 3/1990 | Husted |
| 4,944,745 A | 7/1990 | Sogard et al. |
| 5,040,548 A | 8/1991 | Yock |
| 5,053,033 A | 10/1991 | Clarke |
| 5,061,273 A | 10/1991 | Yock |
| 5,106,360 A | 4/1992 | Ishiwara et al. |
| 5,135,535 A | 8/1992 | Kramer |
| 5,147,377 A | 9/1992 | Sahota |
| 5,154,725 A | 10/1992 | Leopold |
| 5,156,594 A | 10/1992 | Keith |
| 5,171,222 A | 12/1992 | Euteneuer et al. |
| 5,180,367 A | 1/1993 | Kontos et al. |
| 5,199,939 A | 4/1993 | Dake et al. |
| 5,205,822 A | 4/1993 | Johnson et al. |
| 5,226,888 A | 7/1993 | Arney |
| 5,232,445 A | 8/1993 | Bonzel |
| 5,246,437 A | 9/1993 | Abela |
| 5,267,958 A | 12/1993 | Buchbinder et al. |

(List continued on next page.)

FOREIGN PATENT DOCUMENTS

| | | |
|---|---|---|
| DE | 4003 458 A | 8/1991 |
| DE | G9102312.2 | 8/1992 |
| WO | WO92/17236 | 10/1992 |
| WO | WO94/25106 | 11/1994 |
| WO | WO96/14898 | 5/1996 |

*Primary Examiner*—Angela D. Sykes
*Assistant Examiner*—Patricia Bianco
(74) *Attorney, Agent, or Firm*—Gerald W. Spinks

(57) ABSTRACT

A catheter for use with a radioactive source within the catheter to irradiate a selected area of a blood vessel in combination with angioplasty procedures, to prevent restenosis of that area of the blood vessel. The catheter has a guidewire channel formed near its distal end to facilitate use of the catheter as a rapid exchange catheter, allowing insertion of the catheter over a guidewire also used in performance of an angioplasty procedure. The catheter also has a radiation lumen with a sealed end to retain the radioactive source within the catheter. The radiation lumen is sufficiently longer than the guidewire channel to extend into a non-sterile field, keeping the radiation source segregated from the blood, allowing the use of a non-sterile radiation source. The catheter can also be provided with a centering balloon or a set of centering wire loops to center the radioactive source radially within the blood vessel.

3 Claims, 6 Drawing Sheets

U.S. PATENT DOCUMENTS

| | | |
|---|---|---|
| 5,302,168 A | 4/1994 | Hess |
| 5,324,269 A | 6/1994 | Miraki |
| 5,368,567 A | 11/1994 | Lee |
| 5,443,457 A | 8/1995 | Ginn et al. |
| 5,456,680 A | 10/1995 | Taylor et al. |
| 5,503,613 A * | 4/1996 | Weinberger .................... 600/3 |
| 5,540,659 A * | 7/1996 | Teirstein ........................ 600/3 |
| 5,556,389 A | 9/1996 | Liprie |
| 5,618,266 A * | 4/1997 | Liprie ............................ 600/3 |
| 5,643,171 A | 7/1997 | Bradshaw et al. |
| 5,797,948 A | 8/1998 | Duham |
| 5,882,290 A | 3/1999 | Kume |
| 5,891,091 A * | 4/1999 | Teirstein ........................ 600/3 |
| 5,997,571 A | 12/1999 | Farr et al. |
| 6,099,499 A * | 8/2000 | Ciamacco, Jr. ............. 604/103 |
| 6,196,996 B1 * | 3/2001 | Teirstein ........................ 600/3 |

* cited by examiner

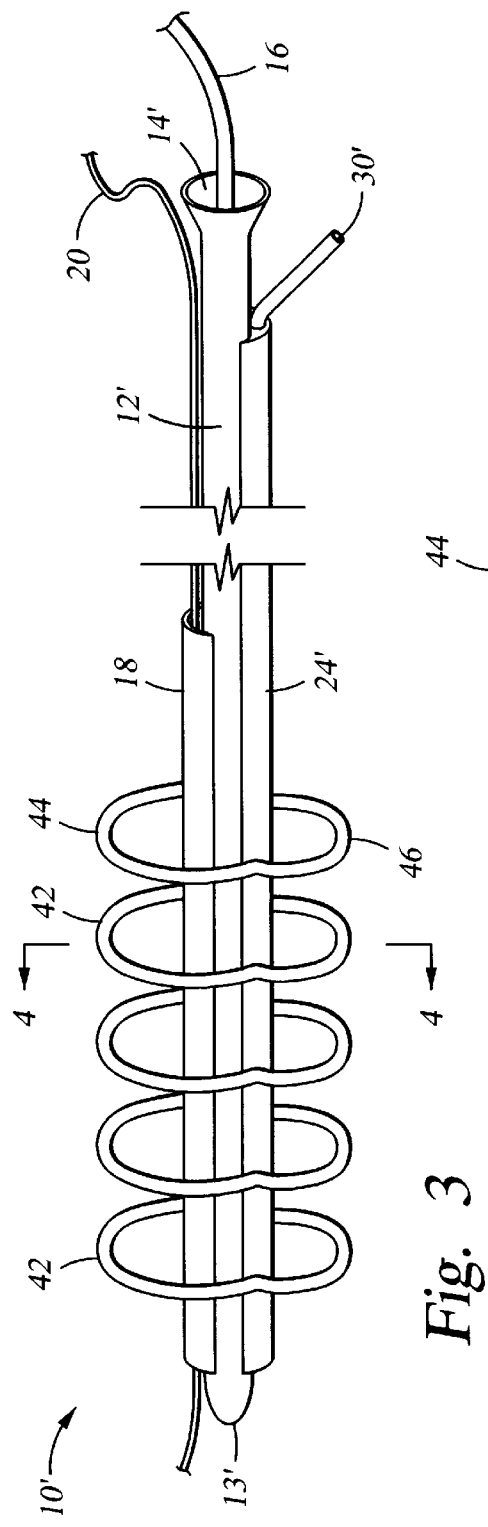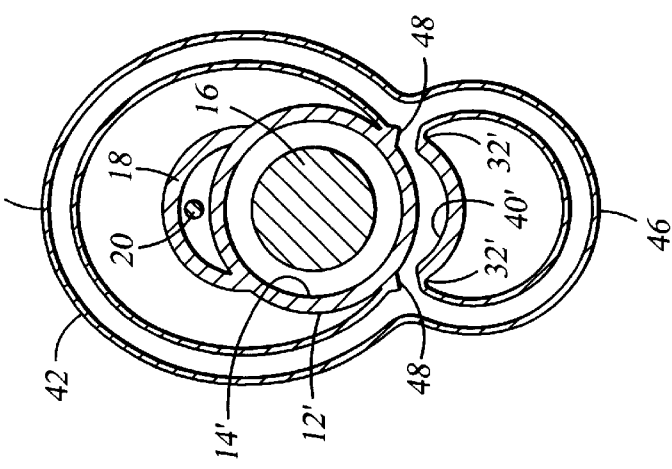

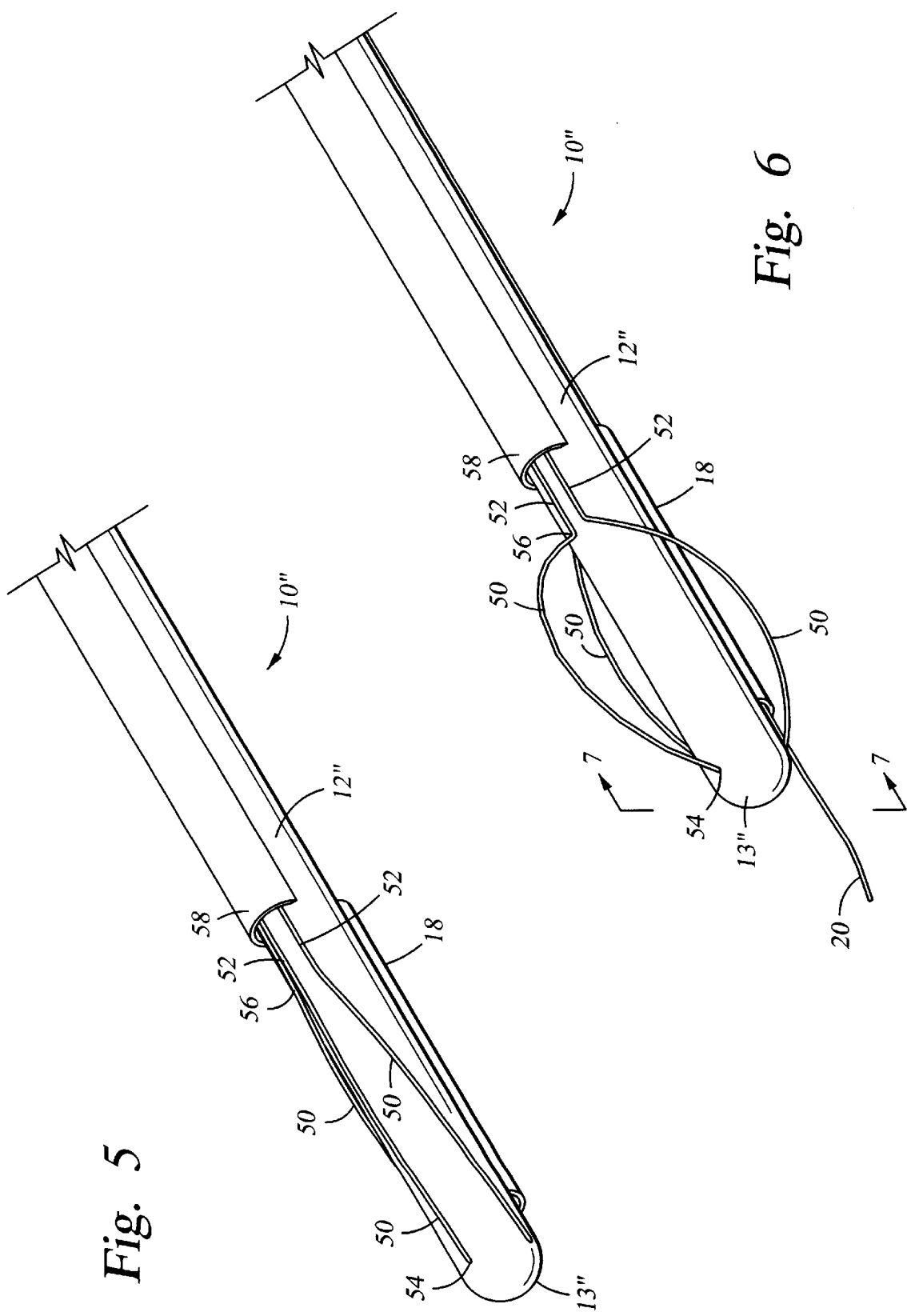

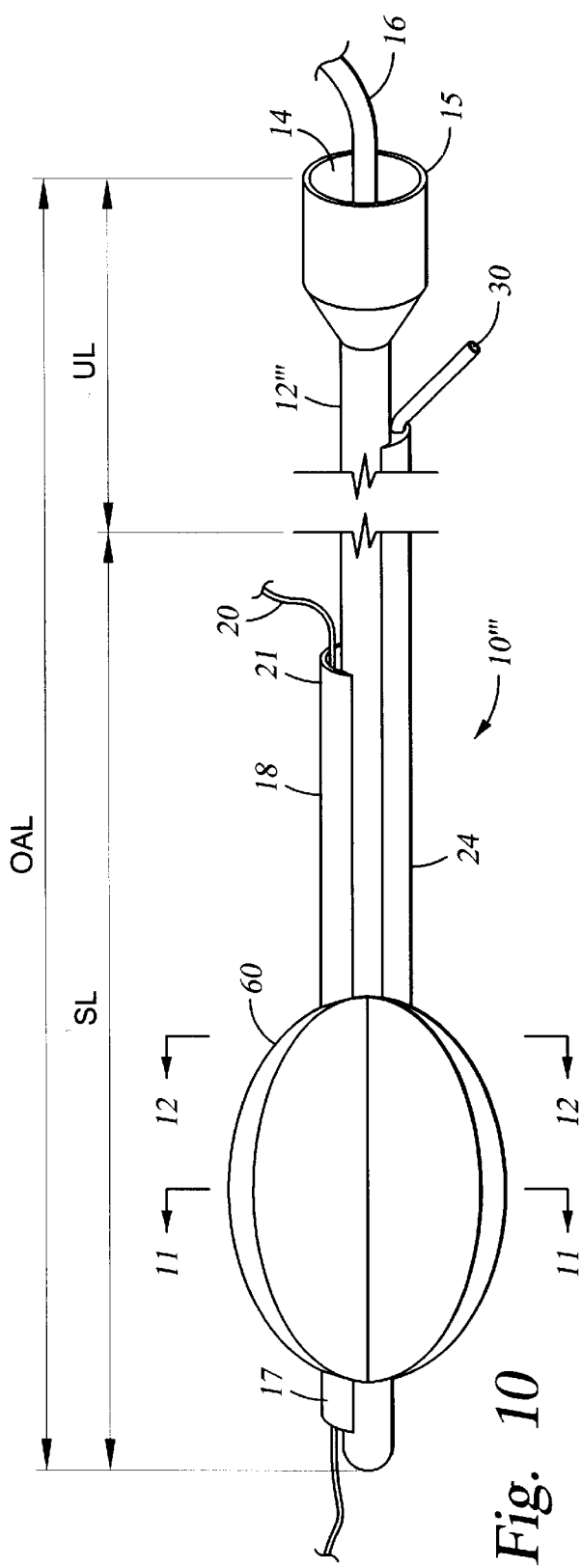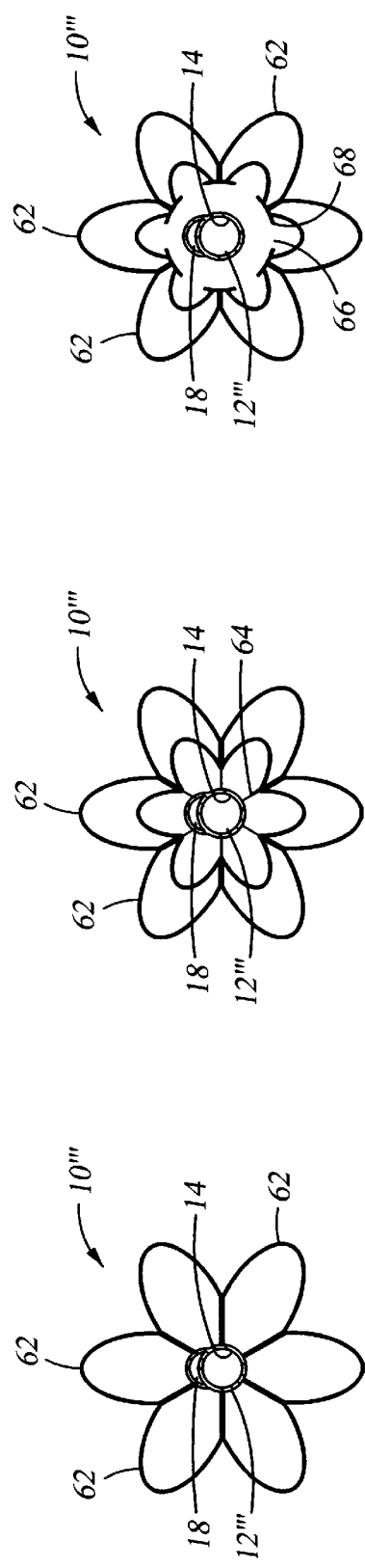

IRRADIATION CATHETER AND METHOD OF USE

CROSS REFERENCE TO RELATED APPLICATIONS

This is a divisional application of U.S. patent application Ser. No. 09/034,138, filed on Feb. 20, 1998 now U.S. Pat. No. 6,196,996, and entitled "Irradiation Catheter and Method of Use", now U.S. Pat No. 6,196,996; which is a continuation-in-part patent application of U.S. patent application Ser. No. 08/643,788, filed on May 6, 1996, now U.S. Pat. No. 5,891,091; which is a continuation of U.S. patent application Ser. No. 08/298,053, filed Aug. 30, 1994, now U.S. Pat. No. 5,540,659; which is a continuation-in-part of U.S. patent application Ser. No. 08/231,423, filed Apr. 22, 1994, now U.S. Pat. No. 5,472,425; which is a continuation-in-part of U.S. patent application Ser. No. 08/197,970, filed Feb. 17, 1994, now U.S. Pat. No. 5,468,225; which is a continuation of U.S. patent application Ser. No. 08/092,332, filed Jul. 15, 1993, now U.S. Pat. No. 5,336,184.

FEDERALLY SPONSORED RESEARCH OR DEVELOPMENT

Not Applicable

BACKGROUND OF THE INVENTION

The present invention is in the field of devices used to subject portions of a blood vessel to nuclear radiation to prevent restenosis of the irradiated area after performance of an angioplasty procedure.

A common problem after performance of a percutaneous transluminal coronary angioplasty is the restenosis of the treated area. In fact, restenosis occurs in 30% to 50% of cases. Restenosis occurs, at least in part, as a result of vascular smooth muscle cell migration, proliferation, and neointima formation at the site of the angioplasty. It has been shown that intracoronary delivery of ionizing radiation causes focal medial fibrosis, which when delivered at the site of the angioplasty, impedes the restenosis process. Adjacent coronary segments and the surrounding myocardium are undamaged by the irradiation treatment.

Delivery of the ionizing radiation at the site of the stenosis can be achieved by the introduction of an irradiation source, such as a ribbon, through an infusion catheter. In known systems, the infusion catheter is inserted to the site of the stenosis over a guidewire which may be inserted before, or alternatively, left after, the performance of an angioplasty procedure. After insertion of the infusion catheter, the guidewire is removed from the catheter, and the irradiation ribbon is inserted in its place. The irradiation ribbon typically incorporates a plurality of Iridium-192 seeds or pellets near its distal end. Other sources that might not be line sources of ionizing radiation can be used, as well. This plurality of radioactive sources arranged essentially in a line approximates a line source, although the intensity of the radiation will vary axially to some extent, depending upon the spacing and length of the seeds. The irradiation ribbon is inserted to the point where the radioactive material is placed in the area of the stenosis. The Iridium-192 emits gamma radiation having a range of energies between 296 and 612 thousand electron volts (keV).

The currently known systems have several disadvantages. First, the guidewire must be withdrawn before insertion of the irradiation ribbon. Withdrawal of the guidewire is not favored by physicians because it adds at least one step to the procedure, and because it takes additional time. The performance of any additional step presents additional opportunities for complications. Time is of the essence during angioplasty because much of the procedure involves at least partial blockage of the flow of blood in the blood vessel, which can be harmful to the muscle served by the vessel. This problem is compounded during the irradiation procedure, since the radioactive source must often be left in place for several minutes in order to deliver the desired dose of radiation to the vascular tissue. The time problem can be further compounded by the need to reinsert the guidewire after delivering the radiation, in some cases. In solving the problem of guidewire placement, it must be kept in mind that the irradiation catheter is often used in very small blood vessels, so it can be desirable to keep the overall diameter of the catheter as small as possible.

A second disadvantage of known systems is that the irradiation ribbon is exposed to blood flow in the infusion catheter, and it is even possible that some of the radioactive seeds could be lost out the distal end of the infusion catheter, or the irradiation ribbon itself can break, releasing radioactive material into the blood. Even if the blood does not directly contact the radioactive material, if blood contacts the radiation source, or if the radiation source enters the sterile field on the operating table, the radiation source must be sterilized. This adds expense to the procedure, and it exposes sterilization personnel to ionizing radiation.

A third disadvantage of known systems is that location of the radioactive material radially within the blood vessel is largely uncontrolled. Rotation of the infusion catheter may assist in centering the radiation source within the stenosis, in some cases, but this method is not always effective. Centering of the radioactive material within the tissues injured by the angioplasty may be required, because it is important to deliver a known dose of radiation uniformly to the affected tissue. The intensity of gamma or beta radiation emanating from a [line] source varies inversely with the square of the radial distance from the source. Therefore, if the radiation source is not centered within the blood vessel, the dose delivered to one side of the vessel can vary greatly from the dose delivered to the opposite side. In addition, if the line source lies at an angle to the centerline of the vessel, rather than being concentric therewith, or at least parallel thereto, the dose delivered can vary axially by an appreciable amount, throughout the length of the stenosis. In some cases, it can even be desirable to position the radiation source parallel to, but offset from, the centerline of the blood vessel, if it is desired to irradiate one side of the stenosis more than the other side. This can be desirable if restenosis is expected to result more from proliferation of the tissues on one side than on the far side.

It is an object of the present invention to provide a catheter assembly for irradiation of a stenotic segment of a blood vessel, which can be inserted to the site of the stenosis over a guidewire. It is a further object of the present invention to provide a catheter assembly which can place an irradiation source at a desired location within a blood vessel, both axially and radially. It is a still further object of the present invention to provide a catheter assembly which allows the safe use of an unsterilized radiation source. It is a yet further object of the present invention to provide an irradiation catheter assembly which has a minimum overall diameter. Finally, it is an object of the present invention to provide a catheter assembly which is economical to manufacture and easy to use.

BRIEF SUMMARY OF THE INVENTION

A summary of the preferred embodiment of the present invention follows for exemplary purposes. The present invention provides a catheter for use with an irradiation source, such as a ribbon, with the catheter being constructed to be inserted over a guidewire which is in place in the blood vessel. The catheter body has a radiation lumen into which the irradiation ribbon, or other radiation source, is inserted. The radiation lumen is sealed at the distal end of the catheter body to fully retain the irradiation ribbon and its incorporated radioactive material.

A guidewire channel is formed on the catheter body, separate from the radiation lumen, with at least a portion of the guidewire channel being formed near the distal end of the catheter body. In a first embodiment, the guidewire channel can be formed as a channel alongside the distal portion of the catheter body. In this first embodiment, the guidewire channel can be sufficiently long to reach the area of the stenosis while also passing through a guide catheter O-ring. A guidewire channel of this length provides a structure surrounding the guidewire, to allow sealing by a guide catheter O-ring. This first embodiment allows the irradiation catheter to be used through a guide catheter, providing a proximal fluid tight sealing surface against which the guide catheter O-ring can seal to allow injection of dye to aid in visualization of the radiation source, while simultaneously allowing free guidewire movement which can help position the irradiation catheter, as will be discussed below. Still further, this first embodiment of the guidewire channel can be formed with a lengthwise rupturable membrane. This essentially provides a distal portion of the guidewire channel for rapid exchange purposes, and a proximal portion of the guidewire channel for sealing purposes. In a second embodiment, the guidewire channel can be formed as only a short segment at the distal end of the irradiation catheter, beyond the distal end of the radiation lumen, allowing the use of the irradiation catheter as a rapid exchange catheter, as described in the patent applications cited earlier, upon which this application relies for priority. This second embodiment minimizes the overall diameter of the catheter, because the guidewire channel is not alongside the radiation lumen at any location. In both the first and second embodiments, the radiation lumen extends in a proximal direction beyond the proximal end of the guidewire channel. This proximal extension of the radiation lumen has a length sufficient to allow the proximal end of the radiation lumen to be handed outside the sterile field, into a non-sterile field, for insertion of the radiation source, while the proximal end of the guidewire channel remains within the sterile field. This allows use of a non-sterile radiation source, avoiding the necessity for sterilization, thereby saving sterilization costs, and eliminating radiation exposure of sterilization personnel.

Since it may be desirable to position the radiation source radially within the blood vessel, at least two methods, as well as several types of apparatus, are provided for accomplishing the radial positioning. A first method can be employed without any special apparatus, by introducing one or more bends in the guidewire, near its distal end. When the catheter and the irradiation ribbon are axially in place in the area of the stenosis, if the distal end of the catheter is not radially positioned as desired, the guidewire can be rotated to orient the bent portion of the guidewire in the direction in which it is desired to displace the catheter. Then, the guidewire can be slightly withdrawn, pulling one or more bends back into the distal end of the guidewire channel. The bend in the guidewire can cause the guidewire to exert a force against the wall of the guidewire channel, resulting in the desired flexing of the catheter body in the direction of the force, placing the distal end of the catheter in the desired radial location.

To implement an alternative method of use, the catheter may also be provided with a means for positioning the radiation source radially within the blood vessel. Most often, this positioning means will be used to center the radiation source radially. The irradiation catheter of the present invention can be used either with or without the positioning means. The positioning means can have various configurations, two examples of which are inflatable balloons and expandable wire loops. An inflatable balloon can be formed as a coil, or as a plurality of essentially annular balloons, or as a plurality of longitudinal lobes. The balloon or balloons can be connected to an inflation lumen formed on the catheter body, for inflation purposes.

Alternatively, a plurality of flexible wire loops can be mounted near the distal end of the catheter body, with one end of each loop fixedly attached to the catheter body, and one end free. The wire loops can be shaped to be self expanding when released, or the free end of each loop can be attached to an expansion means which is movable longitudinally by the user to move the free ends of the wire loops toward the attached ends. This movement causes the loops to expand outwardly. The loops can be mounted at spaced intervals about the periphery of the catheter body, to center the catheter within the blood vessel upon expansion. The expansion means can be relatively stiff wires designed to push on proximally located free ends of the wire loops, or they can be wires designed to pull on distally located free ends of the wire loops. Self expanding wire loops would expand without the aid of such expansion means, upon withdrawal of a retaining sheath.

The novel features of this invention, as well as the invention itself, will be best understood from the attached drawings, taken along with the following description, in which similar reference characters refer to similar parts, and in which:

BRIEF DESCRIPTION OF THE DRAWINGS

FIG. 3 is a perspective view of a second embodiment of an irradiation catheter according to the present invention;

FIG. 4 is a sectional view of the catheter shown in FIG. 3, taken at the line 4—4;

FIG. 5 is a perspective view of a third embodiment of an irradiation catheter according to the present invention;

FIG. 6 is a perspective view of the catheter shown in FIG. 5, with the wire loops in the expanded position;

FIG. 10 is a perspective view of a third embodiment of the irradiation catheter according to the present invention, having a radial positioning balloon;

FIG. 11 is a sectional view of the middle and distal portions of the balloon of the irradiation catheter shown in FIG. 10, taken at the line 11—11;

FIG. 12 is a sectional view of the proximal portion of the balloon of the irradiation catheter shown in FIG. 10, taken at the line 12—12; and FIG. 13 is a sectional view of the proximal portion of an alternative embodiment of the balloon of the irradiation catheter shown in FIG. 10.

DETAILED DESCRIPTION OF THE INVENTION

Figure 1:
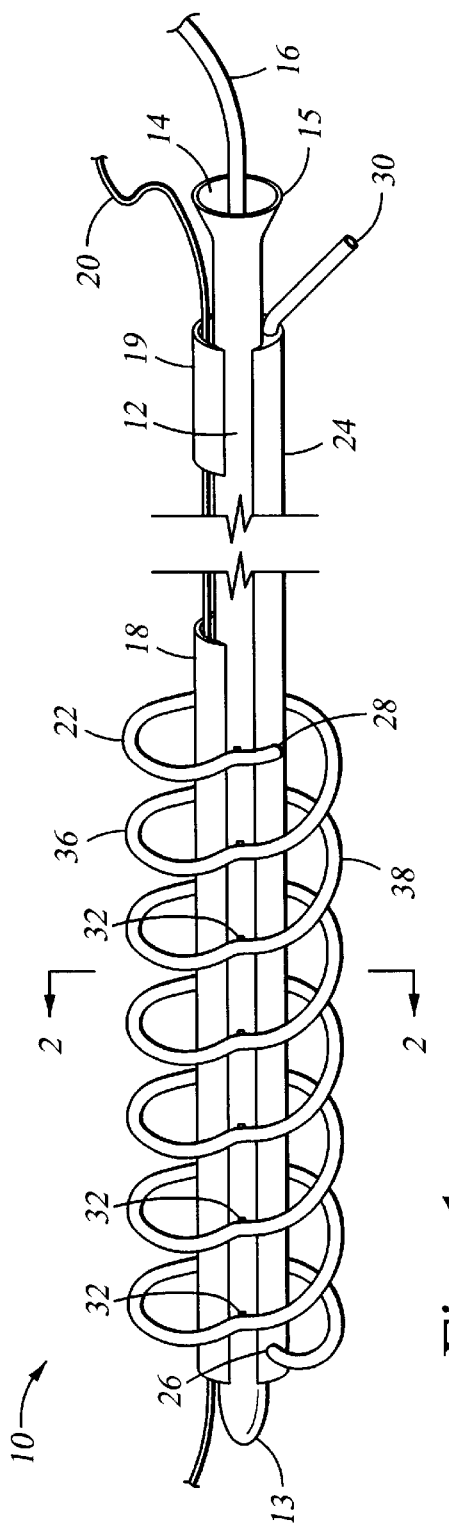
FIG. 1 is a perspective view of a first embodiment of an irradiation catheter according to the present invention.
Figure 2:
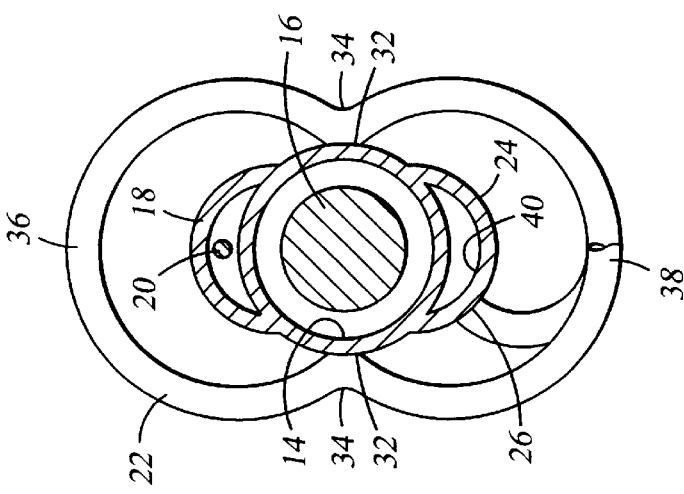
FIG. 2 is a sectional view of the catheter shown in FIG. 1, taken at the line 2—2.

As seen in FIGS. 1 and 2, a first embodiment of the irradiation catheter assembly 10 according to the present invention consists generally of a catheter body 12 having an inner radiation lumen 14 which is closed at a distal end 13, an irradiation ribbon or other source 16 insertable within the inner radiation lumen 14, a distal guidewire channel 18 for guiding the catheter body 12 along a guidewire 20, a proximal guidewire channel 19 for sealing against a guide catheter O-ring, a coil shaped centering balloon 22, and an inflation lumen 24 to which the centering balloon 22 is attached. Several of these elements can have different forms in other embodiments, and some of these features may or may not be present in an irradiation catheter according to the present invention, as will be explained.

The catheter body 12 is an elongated, hollow, flexible, tubular catheter preferably constructed of a plastic material. The proximal end 15 of the catheter body 12 has an open flared port to facilitate insertion of an irradiation ribbon 16 into the radiation lumen 14. The irradiation ribbon 16 can be sized to essentially fill the radiation lumen 14 to position the irradiation sources concentrically with the catheter body 12. The distal end 13 of the catheter body 12 is closed and sealed to retain the irradiation ribbon 16 and its radioactive material.

A guidewire channel 18 is formed on the catheter body 12 separately from the radiation lumen 14. The guidewire channel 18 can be formed as a duct affixed to the wall of the catheter body 12 as shown, or it can be formed inside the radiation lumen 14, or it can be formed as a lumen passing within a thick catheter wall. The guidewire channel portion 18 shown is formed only near the distal end of the catheter body 12, facilitating the use of the catheter body 12 as a rapid exchange catheter by inserting the proximal end of an in-place guidewire 20 through the guidewire channel portion 18, followed by insertion of the catheter body 12 into the patient over the in-place guidewire 20.

Optionally, a second guidewire channel portion 19 essentially like the distal guidewire channel portion 18 can be formed on the catheter body 12 closer to its proximal end 15 to provide a sealing surface for a guide catheter O-ring (not shown) if dye injection is to be used. Sealing against the O-ring is achieved without restricting guidewire movement. The proximal guidewire channel portion 19 is placed so that its distal end is closer to the distal end 13 of the catheter body 12 than the length of the guide catheter being used. This insures that, when the distal end 13 of the catheter body 12 reaches the distal end of the guide catheter, the guide catheter O-ring encircles the proximal guidewire channel 19.

A similar advantage can be achieved by making the guidewire channel 18 run the full length of the catheter body 12, with a lengthwise rupturable membrane formed in the wall of the channel (not shown). This essentially provides a distal guidewire channel portion and a proximal guidewire channel portion, which in this case are formed as parts of a single channel. These portions of the guidewire channel can be used as separate channels, because of the incorporation of the rupturable membrane. Use and construction of such catheters are fully disclosed in the drawings and specifications of several of the aforementioned patent applications, upon which this application is based, and which are incorporated herein for reference.

A centering balloon 22 in the form of a coil is attached to the catheter body 12. This attachment can be at a plurality of attachment points 32 spaced along both sides of the catheter body 12, or it can be a continuous attachment. The attachment points 32 are surface attachments, such as by solvent bonding or ultrasonic welding, and they do not establish flow communication between the balloon coil 22 and the radiation lumen 14. The centering balloon coil 22 is shown in the inflated condition. When the balloon coil 22 is deflated for insertion or withdrawal, it lies essentially flat against the catheter body 12. When inflated, the balloon coil 22 assumes a lobed shape drawn inwardly as shown at points 34, adjacent to the attachment points 32. This creates two extremities or lobes 36, 38 for each loop of the balloon coil 22. Any number of lobes could be used, depending upon the intended use of the assembly 10. The lobes 36, 38 are extended equal distances, when inflated, from the catheter body 12 to radially center the catheter body 12, and hence the irradiation ribbon 16, within a blood vessel. If desired to position the radioactive material closer to one side of the blood vessel, a balloon coil 22 can have only one lobe per loop, or one lobe 36 can be made longer than the opposing lobe 38. Similarly, each loop of the balloon coil 22 is shown to have identical lobes 36, 38 to ensure that the catheter body 12 is held parallel to the walls of the blood vessel. If desired to angle the catheter body along the blood vessel to tailor the radiation exposure to a particular stenotic segment, adjacent loops of the balloon coil 22 could be formed with different sized lobes without departing from the spirit of the invention.

The balloon coil 22 is shown attached in flow communication at its distal end 26 and at its proximal end 28 to the inflation lumen 40 inside the inflation channel 24. A single flow connection anywhere along the balloon coil 22 could be used, if desired. The inflation channel 24 is shown formed as a duct on the wall of the catheter body 12, but it could be formed inside the radiation lumen 14 or the inflation lumen 40 could be formed through the catheter wall. The inflation lumen 40 has an inlet 30 where the inflation fluid is introduced.

FIGS. 3 and 4 show another embodiment of the catheter assembly 10' of the present invention, with a catheter body 12', a guidewire channel 18, and an inflation channel 24' much like the first embodiment. The principal difference between the embodiments is that the radial positioning or centering balloon is formed as a plurality of essentially annular balloon rings 42. Each balloon ring 42 has two extremities or lobes 44, 46, which function essentially the same as the lobes 36, 38 on the balloon coil 22 of the first embodiment. Each balloon ring 42 is attached in flow communication to the inflation lumen 40' at a plurality of attachment points 32' spaced along the inflation channel 24'. Flow communication between the interior of the balloon ring 42 and the inflation lumen 40' is by means of a plurality of inflation ports 48 located at the attachment points 32'. Other forms of the positioning balloon in addition to the two shown here could be devised without departing from the present invention.

Figure 7:
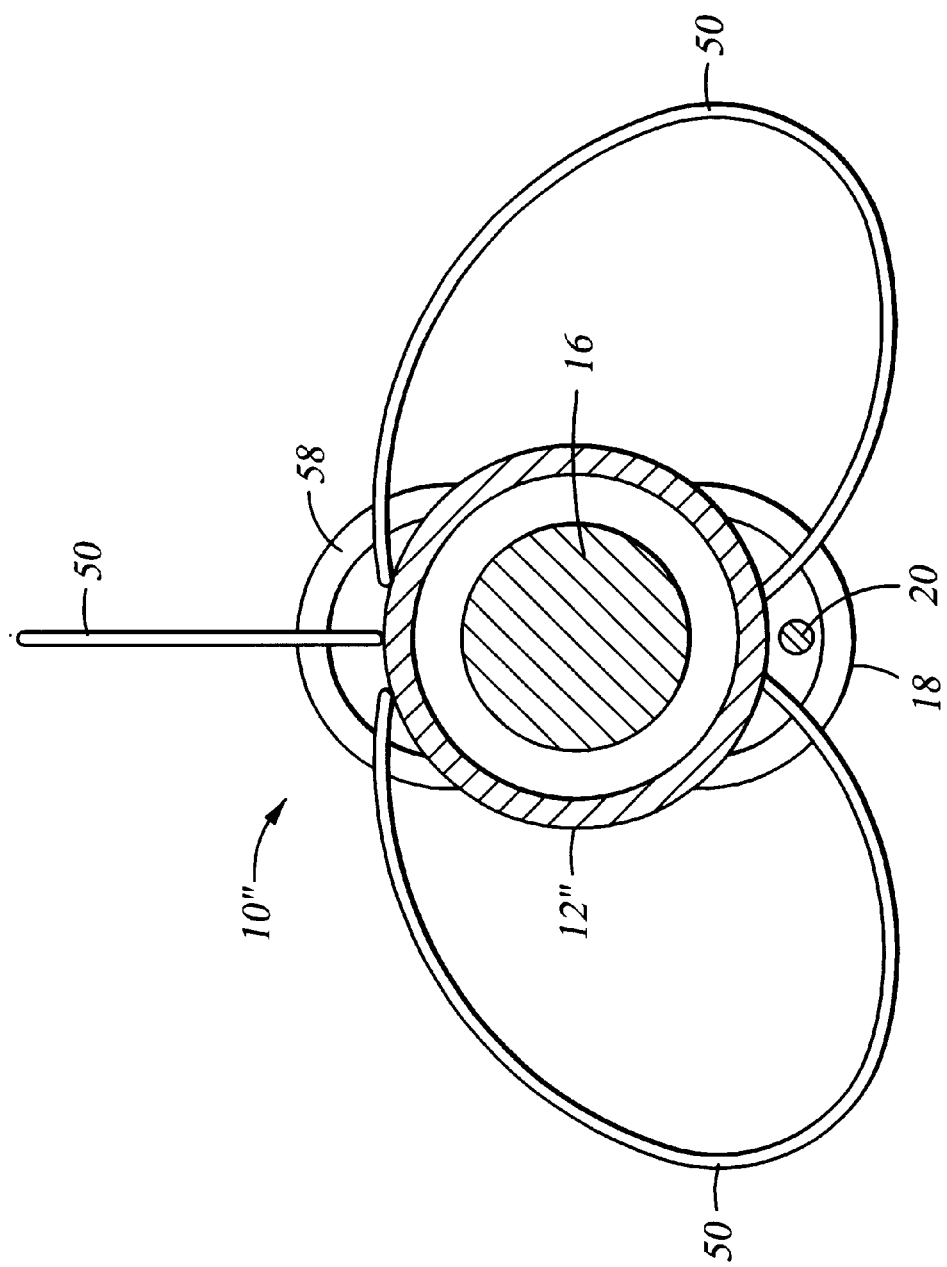
FIG. 7 is a sectional view of the catheter shown in FIG. 6.

Yet another embodiment of the present invention is shown as catheter assembly 10" in FIGS. 5, 6, and 7. A plurality of flexible wire loops 50 are arranged adjacent to the portion of the catheter body 12" where the irradiation source will be located. As seen in FIG. 5, the wire loops 50 are in a contracted condition, with distal ends 54 fixedly attached to the catheter body 12", and with proximal ends 56 free to move relative to the catheter body 12". Each free end 56 is attached to a relatively stiff expansion wire 52, with the plurality of expansion wires 52 passing through an expansion wire guide channel 58 formed on the catheter body 12". The catheter assembly 10" also has a guidewire channel 18, like the first two embodiments. The guidewire is not shown in FIG. 5, for the sake of clarity.

In FIG. 6, the wire loops 50 have been expanded by pushing distally on the expansion wires 52, thereby pushing the free ends 56 of the wire loops 50 toward the attached ends 54. Selective expansion of the wire loops 50 in this way radially positions or centers the catheter body 12" within the blood vessel. Alternatively, the wire loops 50 could have their free ends located near the distal end of the catheter body with the attached ends located proximally, and pulling on the expansion wires could pull the free ends toward the attached ends to expand the wire loops. Further, self-expanding wire loops could be used, with expansion occurring upon withdrawal of a restraining sheath. All of these alternatives are in accordance with the spirit of the present invention, which has the principal attributes described below.

Figure 8:
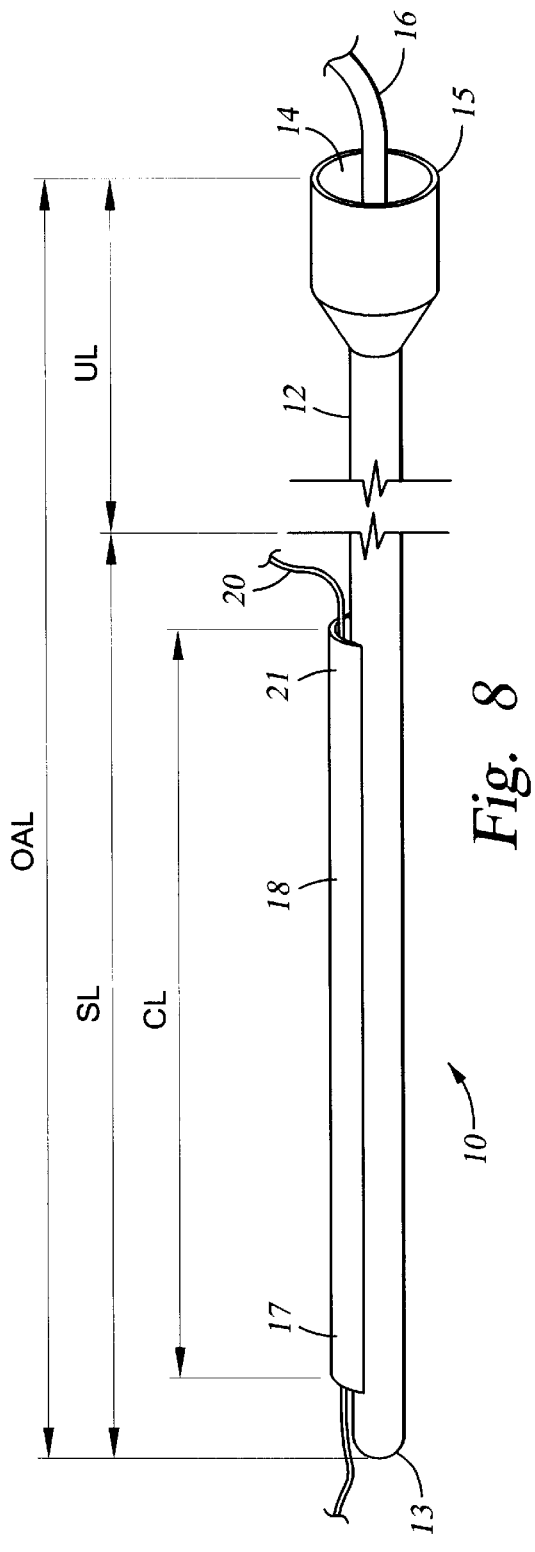
FIG. 8 is a perspective view of an irradiation catheter according to the present invention, showing the proximal extension of the radiation lumen.
Figure 9:
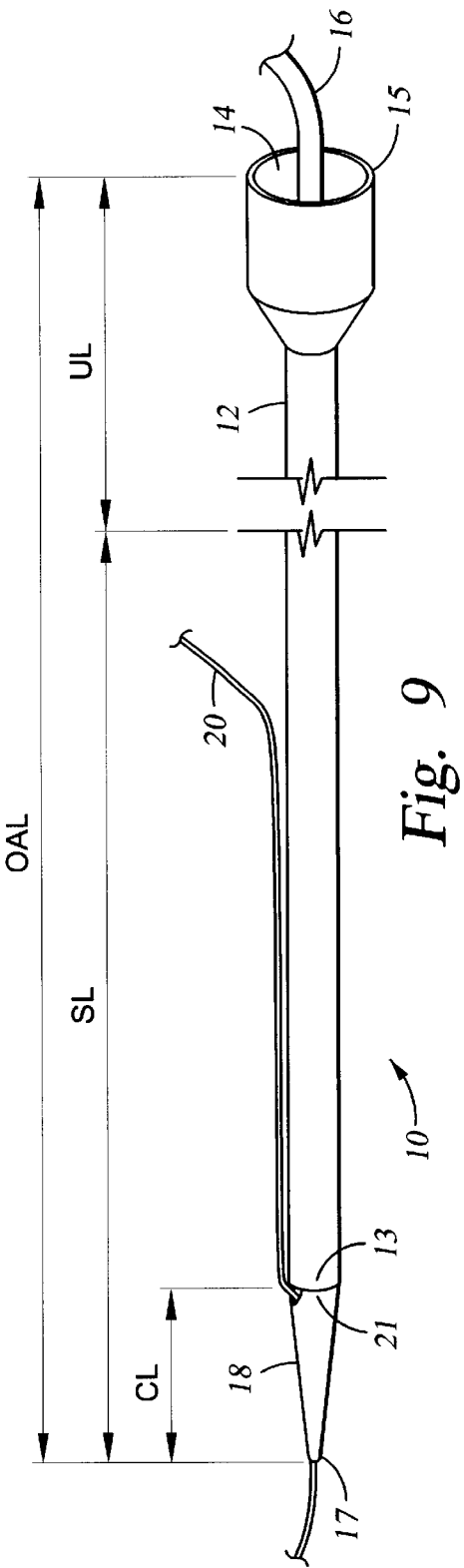
FIG. 9 is a perspective view of another embodiment of the irradiation catheter according to the present invention, having a distally extending guidewire channel.

As shown in FIGS. 8 and 9, the present invention consists generally of a catheter body 12 having an inner radiation lumen 14 which is closed at a distal end 13, and a guidewire channel 18 for guiding the catheter body 12 along a guidewire 20. An irradiation ribbon or other source 16 is insertable within the radiation lumen 14. Several of the other elements discussed above, such as the various radial positioning elements, can be incorporated into the present invention, but they are not shown in FIGS. 8 and 9, which are simplified to illustrate the principal features claimed herein.

The catheter body 12 is an elongated, hollow, flexible, tubular catheter like those discussed above. The proximal end 15 of the catheter body 12 has an open flared port to facilitate insertion of an irradiation ribbon or other source 16 into the radiation lumen 14. The distal end 13 of the catheter body 12 is closed and sealed to retain the irradiation ribbon 16 and its radioactive material.

A guidewire channel 18 is formed on the catheter body 12 separately from the radiation lumen 14. The guidewire channel 18 can be formed as a duct affixed to the wall of the catheter body 12 as shown in FIG. 8, or it can be formed inside the radiation lumen 14, or it can be formed as a lumen passing within a thick catheter wall. Alternatively, the guidewire channel 18 can be attached to the distal end 13 of the catheter body 12, with the entirety of the guidewire channel 18 being completely beyond the distal end 13, as shown in FIG. 9. The guidewire channel 18 shown in both FIGS. 8 and 9 is formed only on a distal portion of the catheter body 12. This facilitates the use of the catheter body 12 as a rapid exchange catheter by inserting the proximal end of an in-place guidewire 20 into the distal end 17 and out the proximal end 21 of the guidewire channel 18, followed by insertion of the catheter body 12 into the patient over the in-place guidewire 20.

The embodiment shown in FIG. 8 has the advantage of possibly providing a sealing surface for the guide catheter O-ring, as discussed above, while the low profile embodiment shown in FIG. 9 has the advantage of having a minimal overall diameter, allowing its use in very small blood vessels. The distal portion SL and the proximal portion UL of each embodiment have relative lengths which yield the advantage of allowing the proximal end 15 of the radiation lumen 14 to be handed outside the sterile field on an operating table without compromising the sterile field, as will be explained more fully below. When taken in combination with the fact that the distal end of the radiation lumen 14 is sealed, this allows the use of an unsterilized radiation source 16, reducing costs and eliminating radiation exposure of sterilization personnel.

In both FIGS. 8 and 9, the distal portion SL of the catheter body 12, including the entirety of the guidewire channel 18, is the portion of the catheter 10 which must be maintained in the sterile field on the operating table. This distal portion SL of the catheter body 12 must be maintained in the sterile field because it is the portion which is exposed to the blood of the patient, either by direct contact with the blood stream, or indirectly by contact with the guidewire 20. The proximal portion UL of the catheter body 12, including the proximal end 15 of the radiation lumen 14, can be handed outside the sterile field into an unsterile field, without compromising the sterile field. This is possible, first, because the distal end 13 of the catheter body 12 is sealed. It is possible, second, because the radiation lumen 14 extends proximally beyond the proximal end 21 of the guidewire channel 18 by a sufficient length to allow manipulation of the proximal end 15 within the unsterile field without re-entering the sterile field. During this manipulation, the distal portion SL can be thought of as roughly representing the "sterile length" of the catheter body 12, while the proximal portion UL can be thought of as roughly representing the "unsterile length". It should be remembered, though, that these terms are only used here for convenience in discussing the relative lengths of these two portions of the catheter 10. In actuality, the sterile or unsterile condition of any particular portion of the catheter body 12, whether the inside surface or the outside surface thereof, depends upon the procedure being followed by the physician. As a procedure progresses, the actual "unsterile length" of the catheter body 12 depends upon how much of the catheter 10 has been passed into the unsterile field.

Importantly, because of the construction of the catheter 10 of the present invention, and because of the relative lengths provided for the "sterile length" SL and the "unsterile length" UL, the irradiation source 16 can be maintained entirely within the unsterile field at all times. When the proximal portion UL of the catheter body 12 is handed into the unsterile field from the sterile field, the outer surface of the proximal portion UL of the catheter body 12 becomes part of the unsterile field. In addition, the entirety of the inner surface of the radiation lumen 14 becomes part of the unsterile field, since the unsterile irradiation source 16 is inserted into the radiation lumen 14 from the proximal end 15, which is in the unsterile field. Therefore, even the portion of the inner surface of the radiation lumen 14 which extends into the patient is part of the unsterile field. Of course, the unsterile field is isolated from the patient by the wall of the catheter body 12 and its sealed distal end 13. This allows use of an unsterilized irradiation source 16.

It is important for the proximal portion UL of the catheter body 12 to be sufficiently long to allow the manipulation of its proximal end 15 while inserting and retrieving the radiation source 16, without the risk of allowing the proximal end 15 to re-enter the sterile field. It has been found that in the performance of the typical irradiation procedure, a length of approximately 100 to 120 centimeters of the proximal portion UL of the catheter body 12 allows safe manipulation of the proximal end 15 without risking re-entry of any of the proximal portion UL into the sterile field. Of course, this is not an exact length. It is simply indicative of an approximate preferred length, and any length which is an order of magnitude smaller would be too short, while any length which is an order of magnitude greater would be excessive.

A typical irradiation catheter 10 incorporating the present invention might have an overall length OAL of approximately 240 centimeters, with a "sterile length" SL of approximately 140 centimeters, and an "unsterile length" UL of approximately 100 centimeters. In the embodiment shown in FIG. 8, the guidewire channel 18 of such a catheter 10 could have a length CL up to approximately 130 centimeters. In the low profile embodiment shown in FIG. 9, the guidewire channel 18 of such a catheter 10 could have a length CL of approximately 2 centimeters.

FIGS. 10 through 13 show yet another embodiment of the invention claimed herein. As shown in FIG. 10, this embodiment of the irradiation catheter 10''' consists generally of a catheter body 12''' having an inner radiation lumen 14 which is closed at a distal end 13, and a guidewire channel 18 for guiding the catheter body 12 along a guidewire 20. An irradiation ribbon or other source 16 is insertable within the radiation lumen 14. The catheter body 12''' is an elongated, hollow, flexible, tubular catheter like those discussed above. The proximal end 15 of the catheter body 12''' has an open flared port to facilitate insertion of an irradiation ribbon or other source 16 into the radiation lumen 14. The distal end 13 of the catheter body 12''' is closed and sealed to retain the irradiation ribbon 16 and its radioactive material.

In this embodiment, the catheter 10''' includes a centering or positioning balloon 60 mounted on the periphery of the catheter body 12''', near its distal end 13. As shown in FIGS. 10 through 13, the balloon 60 can consist of a plurality of lobes 62 extending radially from the 10 catheter body 12'''.

A guidewire channel 18 is formed on the catheter body 12''' separately from the radiation lumen 14. At the midpoint and the distal portion of the balloon 60, the guidewire channel 18 can be formed as a duct affixed to the wall of the catheter body 12''', between two of the balloon lobes 62, as shown in FIG. 11. At the proximal portion of the balloon 60, the guidewire channel 18 can be formed as a duct affixed to the wall of the catheter body 12''', between two of the balloon lobes 62 as shown in FIG. 12, or it can be formed inside an inflation manifold 68, as shown in FIG. 13. FIG. 11 shows a sectional view taken through the midpoint of the balloon 60, to illustrate the placement of the guidewire channel 18. A sectional view of the distal portion of the catheter 10''' would be essentially the same as FIG. 11. FIG. 12 shows a sectional view taken through the proximal portion of the balloon 60, to illustrate the placement of both the guidewire channel 18 and one means for inflating all of the lobes 62 of the balloon 60. Rather than having the lobes 62 attached to the catheter body 12''', in the proximal portion of the balloon 60, inflation ports 64 are positioned between the lobes 62. This allows inflation fluid introduced into a proximal end of any one lobe 62 via the inflation channel 24 to flow into all of the other lobes 62, thereby inflating them. FIG. 13 shows an alternate means for inflating all of the lobes 62. An annular inflation manifold 68 is situated in the proximal portion of the balloon 60, surrounding the catheter body 12'''. The inflation manifold 68 provides a connection surface for all of the lobes 62. A plurality of inflation ports 66 are provided in the inflation manifold 68, to introduce inflation fluid into each lobe 62.

The method of use of the apparatus of the present invention will now be described. Reference to any embodiment of the catheter assembly, catheter body, inflation channel, or positioning means will be intended to refer to all such embodiments. Irradiation could be accomplished either before or after the performance of the angioplasty procedure. In either case, a guidewire 20 will be in place, inserted to the site of the stenosis. If an angioplasty balloon catheter is in place, it can be withdrawn from the guide catheter, leaving the guidewire 20 in place. Working entirely within the sterile field, the physician can insert the proximal end of the guidewire 20 into the distal end 17 of the guidewire channel 18 on the catheter assembly 10 of the present invention. The distal end 13 of the catheter body 12 is then inserted to the site of the stenosis, over the guidewire 20.

The proximal end 15 of the catheter body 12 can be handed out of the sterile field into the unsterile field, along with the proximal portion UL of the catheter body 12. Care should be taken to ensure that a sufficient length of the proximal portion of the catheter body 12 is handed into the unsterile field, while at least the entirety of the guidewire channel 18 is maintained within the sterile field. In the case of the typical 240 centimeter catheter discussed above, approximately 100 centimeters of the proximal portion of the catheter body 12 will be handed into the unsterile field, while approximately 140 centimeters of the distal portion will be maintained in the sterile field. Working entirely within the unsterile field, additional medical personnel can then insert the irradiation ribbon 16 into the catheter body 12 after the catheter body 12 is in place. Maintaining the guidewire channel 18 entirely within the sterile field allows the aseptic manipulation of the guidewire 20.

If the embodiment in use incorporates the proximal guidewire channel 19 or the full length channel with the rupturable membrane, the guide catheter O-ring can be tightened sealingly around the proximal end of the catheter body 12 to facilitate the injection of dye while allowing free guidewire movement. This aids in visualization of the radiation source for positioning purposes. Furthermore, use of the proximal guidewire channel 19 or the full length channel permits free movement of the guidewire relative to the catheter body as described earlier. If the embodiment incorporating the positioning means is used, when the radioactive seeds are in place within the dilated area of the blood vessel, inflation fluid is introduced into the inflation channel and pressurized to inflate the positioning balloon, such as the balloon coil 22, the balloon rings 42, or the lobed balloon 60, thereby radially positioning or centering the catheter body 12 within the blood vessel. If the embodiment incorporating wire loop positioning means is used, of course, the expansion wires 52 could be used at this stage to expand the wire loops 50. Alternatively, the positioning means can be activated first, whether a balloon or wire loops are used, followed by insertion of the irradiation ribbon 16.

Instead of using the positioning balloon or the wire loops, it may be desired to use the bent guidewire method of radially positioning the distal end of the catheter body. If the physician observes that the distal end of the catheter body 12, where the irradiation seeds are located, is not positioned radially as desired, the guidewire 20 is first rotated to orient a bend near the distal end of the guidewire 20 as desired. The bend can be a relatively gentle bend as shown in FIGS. 1 or 3, or it can be more pronounced, depending upon the physical configuration of the blood vessel and the stenosis being treated. Further, a series of bends might be appropriate. The bends could be introduced into the guidewire 20 prior to original insertion of the guidewire 20, or the guidewire 20 can be withdrawn, bent appropriately, and reinserted, if the catheter in use has a full length guidewire channel. After rotation of the guidewire 20 to orient the bend in the direction of desired deflection of the catheter body 12, the catheter body 12 is held in place longitudinally while the distal end of the guidewire 20 is carefully withdrawn into the distal end of the guidewire channel 18. As the bend on the distal end of the guidewire 20 enters, or begins to enter, the distal end of the guidewire channel 18, the guidewire 20 exerts a transverse force on the wall of the guidewire channel 18. This transverse force is in turn transferred to the distal end of the catheter body 12, causing it to deflect in the desired direction.

Regardless of the method used to radially position the irradiation source 16, the source is then left in place until the desired dose has been administered. After leaving the irradiation source 16 in place for the desired length of time to achieve the desired radiation dose, the irradiation source 16 is withdrawn into the unsterile field. Then, because the guidewire channel 18 has been maintained entirely within the sterile field, the catheter assembly 10 can be withdrawn, leaving the sterile guidewire 20 in place for insertion of an angioplasty catheter or for the accomplishment of other procedures as required.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

I claim:

1. A method for irradiating a stenotic segment of a blood vessel having a guidewire disposed therein, said method comprising:

providing an irradiation catheter having a radiation lumen with a closed distal end and having a guidewire channel formed adjacent said distal end of said radiation lumen;

providing an irradiation source;

inserting a proximal end of the guidewire through said guidewire channel;

inserting said irradiation catheter into the blood vessel over the guidewire, until said distal end of said radiation lumen is located within said stenotic segment;

retaining said guidewire channel entirely within a sterile field;

placing a proximal end of said radiation lumen within a non-sterile field;

inserting said irradiation source into said proximal end of said radiation lumen, until said irradiation source is located within said stenotic segment.

2. A method as recited in claim 1, further comprising:

providing said guidewire channel entirely distal of said distal end of said radiation lumen; and inserting said irradiation catheter into the blood vessel until said guidewire channel is located distal of said stenotic segment.

3. A method as recited in claim 1, further comprising:

providing said guidewire channel alongside a distal portion of said radiation lumen; and inserting said irradiation catheter into the blood vessel until a portion of said guidewire channel is located within a guide catheter.

* * * * *